United States Patent [19]

Neukom et al.

[11] Patent Number: 5,057,539
[45] Date of Patent: Oct. 15, 1991

[54] MOTH- AND BEETLE-PROOFING AGENTS

[75] Inventors: Alfred J. Neukom, Kienberg, Switzerland; Dieter Reinehr, Kandern, Fed. Rep. of Germany; Werner Schmid, Riehen, Switzerland

[73] Assignee: Ciba-Geigy Corporation, Ardsley, N.Y.

[21] Appl. No.: 512,710

[22] Filed: Apr. 23, 1990

Related U.S. Application Data

[62] Division of Ser. No. 271,962, Nov. 16, 1988, abandoned.

[30] Foreign Application Priority Data

Nov. 24, 1987 [CH] Switzerland ............... 4559/87

[51] Int. Cl.$^5$ ............ A01N 47/28; A01N 53/00
[52] U.S. Cl. ............................ 514/531; 514/598; 514/521
[58] Field of Search ............................ 514/531, 598

[56] References Cited

U.S. PATENT DOCUMENTS 4,219,593 8/1990 Muntwyler et al. ............ 428/15

FOREIGN PATENT DOCUMENTS 941269 11/1963 United Kingdom ............... 514/598

OTHER PUBLICATIONS

S. W. Carter et al., J. Textile Inst., 67, No. 3 (1976).
Worthing et al.; The Pesticide Manual, 8th Ed. (1987), pp. 647–648.

Primary Examiner—Allen J. Robinson
Attorney, Agent, or Firm—Edward McC. Roberts

[57] ABSTRACT

An agent for proofing keratinous material against attack by pests that feed on keratin, which contains as active compound at least one diphenylurea of the formula

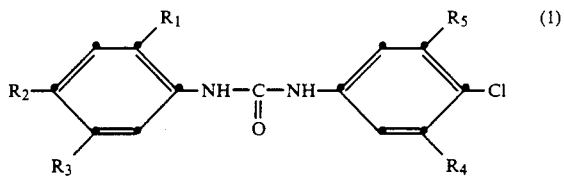

and one synthetic pyrethroid and also, if desired, further auxiliaries, and also a process for proofing keratinous material against attack by keratin pests.

2 Claims, No Drawings

MOTH- AND BEETLE-PROOFING AGENTS

This is a division of application Ser. No. 271,962 filed Nov. 16, 1988, now abandoned.

The present invention relates to an agent for proofing keratinous material, such as, in particular, wool, furs and feathers, against attack by pests that feed on keratin, such as, in particular larvae of moths and beetles, and also to a process for proofing keratinous material against attack by keratin pests by treating the material to be proofed with the agent according to the invention.

German Patent Specifications 764,891 and 1,003,717 disclose halogenated and also sulfonate derivatives of diphenylurea, which are effective against larvae of the clothes moth and of Anthrenus and Attagenus species. They are therefore suitable for proofing wool, furs and feathers against keratin feeding.

It has also already been disclosed that certain synthetic pyrethroids can be used for controlling pests that feed on keratin. See, for example, J.Text.Inst. Vol. 67 (1976), 77–81, German Offenlegungsschrift 2,923,217, U.S. Pat. No. 4,219,593 and European Patent 11 789. These pyrethroids are mainly effective against moth larvae, whereas their action against larvae of the carpet beetle is low.

It has now been found that an agent containing (A) at least one diphenylurea of the formula

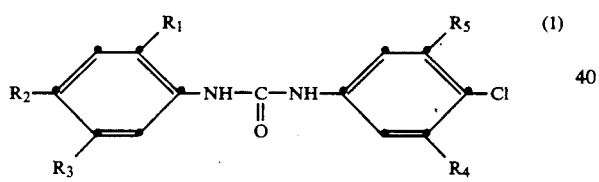

in which $R_1$ is hydrogen or 4-chlorophenoxy-6-sulfonate, $R_2$ is hydrogen or chlorine, $R_3$ is chlorine or trifluoromethyl, $R_4$ is hydrogen or chlorine and $R_5$ is hydrogen or trifluoromethyl, and (B) at least one synthetic pyrethroid, has an excellent proofing action, through a surprisingly synergistic effect, on keratinous materials, in particular on wool, against all keratin pests, in particular larvae of moths and beetles, even when it is only employed in very low concentrations.

The agents according to the invention preferably contain diphenylureas of the formula (2) and/or (3)

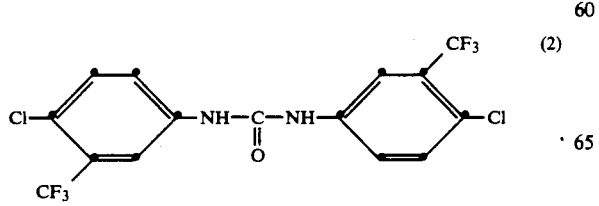

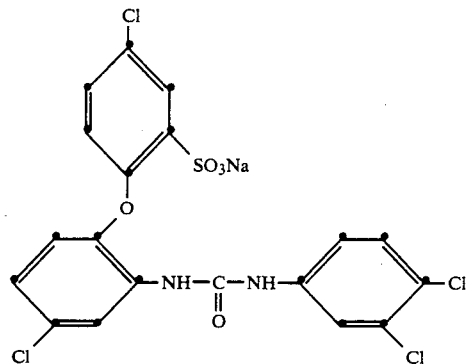

The second component (component B) of the agents according to the invention is a synthetic pyrethroid. Preferred synthetic pyrethroids in agents according to the invention are derived from the class of the cyclopropane-carboxylic acid esters or α-alkyl-(especially isopropyl) phenyl acetic acid esters, i.e. they contain the structural elements

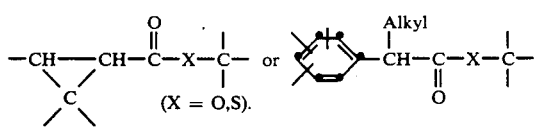

Examples of cyclopropanecarboxylic acid esters employed are compounds of the general formaula

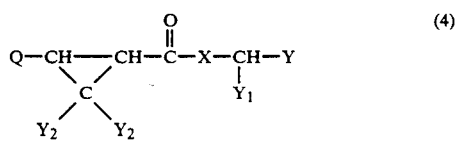

in which Q is $Br_2C=CBr-$,

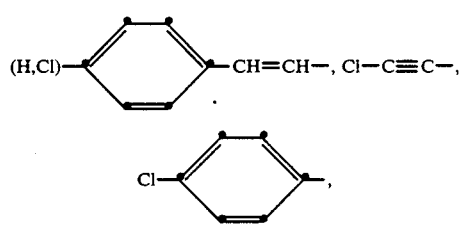

$(CH_3)_3C-O-$,

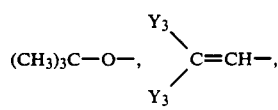

in which $Y_3$ is Cl, Br, F, $CF_3$ or $C_1$-$C_4$alkyl, $CH_2=CH-CH_2-O-$ or T,0045 in which a, b, c and d, independently of one another, are Cl, Br or F, where c and d can also be methyl, X is oxygen or sulphur, $Y_1$ is hydrogen, CN, $CH_3$, $C_2H_5$, i-$C_3H_7$,

-C=CH, -C≡C-CH$_3$, -C≡C-C$_6$H$_5$, -CH=CH-CH$_3$, -CH$_2$-CH=CH$_2$, -CH=CH$_2$ or -CH$_2$-CH=CHCl, Y$_2$ is methyl or both symbols Y$_2$ complete a cyclopropane, cyclobutane or cyclopentane ring and Y is

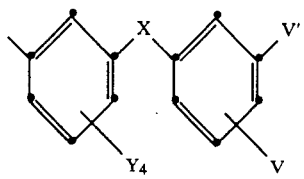

in which Y$_4$ is hydrogen or fluorine and V is hydrogen Cl, Br, F, CH$_3$ or NO$_2$ and V' is hydrogen, where V' can also be CF$_3$ if V is hydrogen, and X is as defined above; Y is also

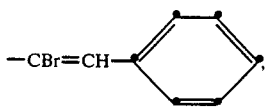

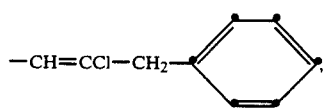

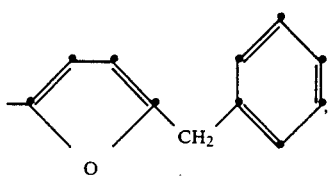

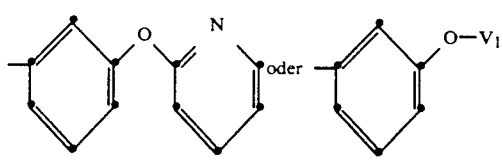

in which V$_1$ is -CH$_2$-CH=CH$_2$, -CH$_2$-C≡CH, -CH$_2$-CH=CH-CH$_3$,

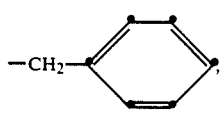

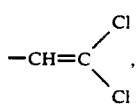

-CF=CFCl or -CF=CF$_2$.

α-alkylphenylacetic acid esters employed are in particular compounds of the general formula

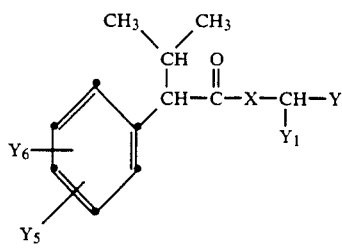

in which X, Y and Y$_1$ are as defined in formula (4), Y$_5$ is hydrogen, CH$_3$, Cl, NO$_2$, OCH$_3$, OCH(CH$_3$)$_2$, =OCH$_2$C≡CH or OCH$_2$CH=CH$_2$ and Y$_6$ is hydrogen, CH$_3$, Cl, Br or F, or Y$_5$ and Y$_6$ in the orthoposition to-gether complete a fused benzene ring, the compounds of the formula (4) being preferably used. Particularly, preferred components (B) which may be employed are those of the above defined formula (4), in which Q is a radical of the formula T,0060
in which Y$^1_3$ is Br, Cl or CH$_3$, X is oxygen and Y is

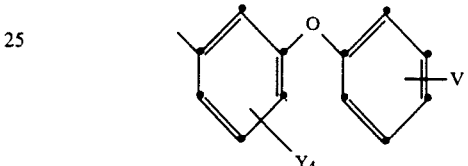

Y$_2$ in formula (4) is preferably CH$_3$ and Y$_1$ is hydrogen, CN, CH$_3$, -CH=CH$_2$, -C≡CH or -C≡CH$_3$, in particular hydrogen or CN.

In particularly interesting agents according to the invention the component (B) is a compound from the class of the 3''-phenoxybenzyl 3-(2',2'-dihalogenovinyl) -2,2-dimethylcyclopropanecarboxylates, in particular one of the formula

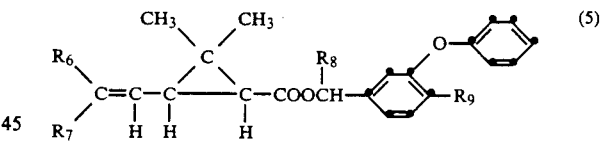

in which R$_6$ is chlorine or bromine, R$_7$ is chlorine, bromine or 4-chlorophenyl, R$_8$ is hydrogen, cyano, -CH=CH$_2$ or -CH≡C-CH$_3$ ànd R$_9$ is hydrogen or fluorine. In addition to component (A) the agents contain, in particular, at least one compound of the formula (6) and/or (7).

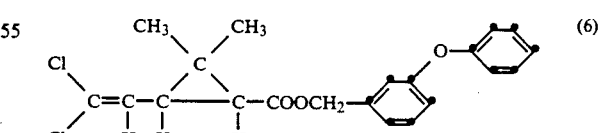

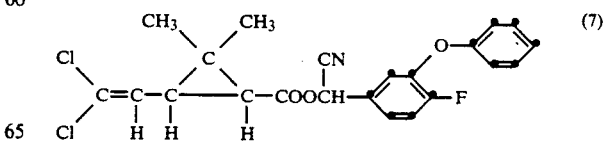

Particularly preferred synthetic pyrethroids (B) are permethrin and cypermethrin.

Particularly preferred agents contain as combination a diphenylurea of the formula

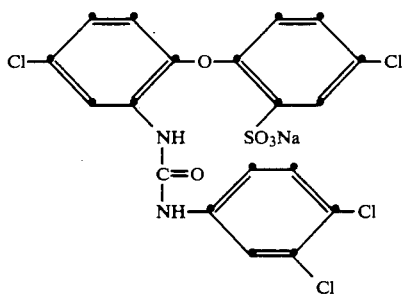
(3)

and as synthetic pyrethroid B, permethrin or a diphenylurea of the formula

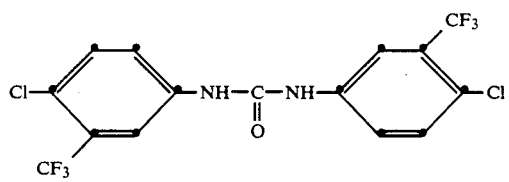
(2)

and as synthetic pyrethroid B, permethrin.

The agents according to the invention can consist exclusively of the components (A) and (B) or they can contain other proofing agents which are effective against insects that feed on keratin, for example, benzimidazoles, aromatic sulfonamides and phosphoric acid esters and phosphonic acid esters. Apart from these the agents can additionally also contain further auxiliaries such as solvents, water, acids, bases, surfactants, wetting agents, dispersants and/or emulsifiers.

Particularly advantageous auxiliaries which lead to a storage-stable, directly usable formulation are described, for example, in EP-A 74 335 (see components C to G). The present invention accordingly also relates to agents which contain components C to G. These components described therein and their preferred representatives and also the relative ratios thereof are stated to be a part of the present description.

The pyrethroids of the formula (4) (component (B)) are known (e.g. DE-A-2,923,217, US-A-4,219,593). The diphenylureas of the formula (1) are also known and can be obtained by processes known per se.

The mixing ratio of the two active compound components (A) and (B) in the agents according to the invention (active compound combinations) can vary within wide limits; it can for example be between 1:1 and 16:1, preferably between 4:1 and 8:1.

The agents according to the invention can be employed for proofing keratinous material against insects that feed on keratin, such as Tineola spec. and Tinea spec. and also against Coleoptera larvae that feed on keratin, e.g. Anthrenus spec. and Attagenus spec.. The agents are most suitable for proofing keratinous or keratin-containing material against feeding damage by insects, in particular for washfast and lightfast treatment against insects, in particular for moth- and beetle-proofing of such materials. Keratinous or keratin-containing material can be proofed both in the raw state and in the processed state, for example raw or processed sheep's wool, products made of other animal hairs, hides, fur and feathers.

Of particular practical importance is the effectiveness and hence the application of the agent according to the invention, in particular of those which contain as compound A a diphenylurea of the formula

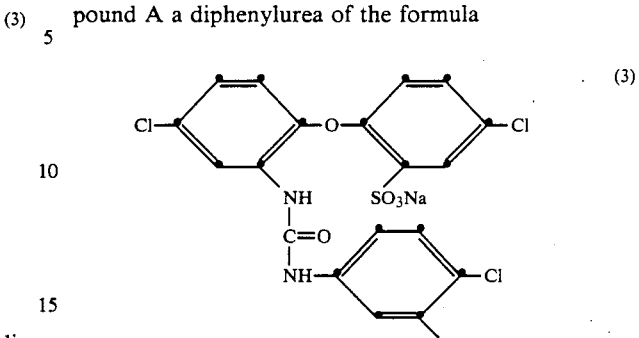
(3)

and as synthetic pyrethroid B, permethrin or which contain as compound A a diphenylurea of the formula

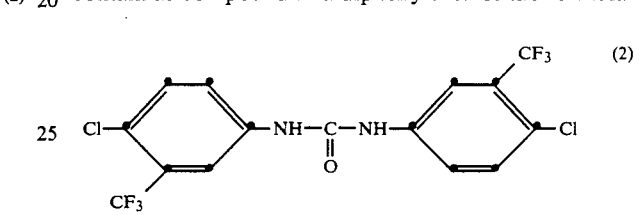
(2)

and as synthetic pyrethroid B, permethrin, against the larvae of the webbing clothes moth (Tineola bisselliella), of the pelt moth (Tinea translucens) and in particular of the seed moth (Hofmannophila pseudopretella) and also against the larvae of fur beetles and carpet beetles (Attagenus spec. and Anthrenus spec. respectively), e.g. of the varied carpet beetle (Anthrenus verbasci), of the pimpernel flower beetle (Anthrenus pimpinellae), of the carpet beetle (Anthrenus scorphilariae), of the carpet beetle (Anthrenus fasciatus), of the fur beetle (Attagenus Pellio) and, in particular, of the black carpet beetle (Attagenus piceus) and of the furniture carpet beetle (Anthrenus vorax).

The agents according to the invention are preferably employed on the one hand for proofing wool textiles, e.g. wool blankets, wool carpets, wool underwear, wool clothing, knits or wool-containing textiles, such as blend fabrics, one component of which is wool, e.g. blend fabrics of wool and other natural fibres, preferably cotton, or of wool and synthetic fibres, on the other hand also for proofing furs and hides against attack by the abovementioned pests.

The present invention also relates to a process for proofing keratinous material, in particular wool textiles, against attack by keratin pests, e.g. larvae of moths and beetles, which comprises treating the material to be proofed with a combination of one or more diphenylureas of the formula (1) and one or more synthetic pyrethroids, preferably those of the formula (6) and (7). For this purpose, this active compound combination which, if desired, can also contain further proofing agents and/or auxiliaries as agent according to the invention, is generally introduced into an application liquor to which further conventional textile auxiliaries and/or dyes can, if desired, be added, and the material to be proofed is impregnated with this liquor. The two active compound components (A) and (B) can of course also be added separately to the application liquor.

The materials to be proofed, in particular textile materials, can, for example, be impregnated using hot or cold aqueous dyeing, bleaching, chroming or aftertreatment baths, which contain a specific amount of an active compound combination according to the invention, various textile finishing processes being possible, for example the pad or exhaust process.

The particular amount employed of an agent according to the invention which is introduced into the particular application bath, depends on the particular substrate and on the method of application. However, this amount is usually dimensioned to be such that, after application to the particular material to be proofed, the latter contains about 10 to 2,000 ppm, preferably 100 to 1,000 ppm of the active substance combination, i.e. of components (A) +(B). For the exhaust process at a liquor to goods ratio of 20:1, for example, this results in concentrations of 0.001 to 1 g of active substance per litre of treatment bath, depending on the degree of exhaustion obtainable. In the pad process concentrations up to 2 g of active substance per litre are possible.

In the following examples, unless otherwise stated, parts and percentages are by weight.

Example 1

2.1 parts of permethrin
5.0 parts of tallow fatty amine ethoxylated with 6-7 mols of ethylene oxide,
25.0 parts of dimethyllaurylamine oxide,
14.5 parts of a block polymer of propylene glycol and ethylene oxide (average molecular weight: 4,900; 80% hydrophobic groups, 20% hydrophilic groups; HLB =4),
7.5 parts of castor oil polyglycol ether,
3.0 parts of alkylphenol polyglycol ether phosphate and
34.5 parts of dimethyl methanephosphonate (DMMP) are mixed. 8.4 parts of the compound of the formula

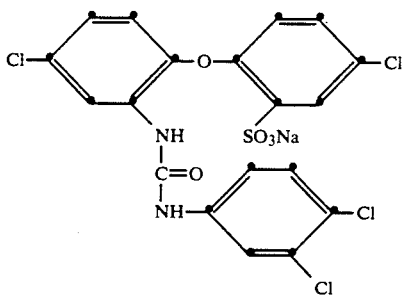

are added to this mixture with continuous stirring at 45-55° C. until a homogeneous formulation is formed. The moth-proofing formulation thus obtained has a long shelf life, is water-miscible and when applied to keratinous material produces excellent moth and beetle-proof finishes.

In the formulation described above permethrin can be replaced by cypermethrin, the compound of the formula (3) can be replaced by the compound of the formula

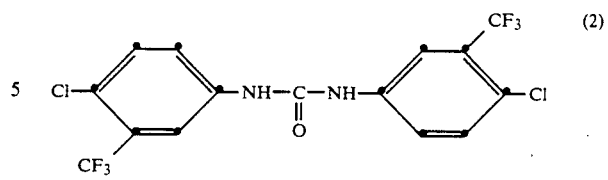

DMMP by N-methyl-2-pyrrolidone, diethylene glycol ethyl ether, ethylpolyglycol or polydioles and/or alkylphenyl polyglycol ether phosphate bu succinic acid, lactic acid, formic acid or acetic acid. This results in formulations having similarly good properties.

The formulations given in the following examples are obtained analogously to example 1, i.e. the components, with the exception of the diphenylurea, are mixed and the latter is subsequently incorporated in the manner described. All of these formulations thus obtained have the required properties, namely long shelf lives, miscibility with water and problem-free application on keratinous materials.

EXAMPLE 2

The formulation of the following compositions is obtained analogously to example 1.

1.2 parts of permethrin,
9.6 parts of the compound of the formula

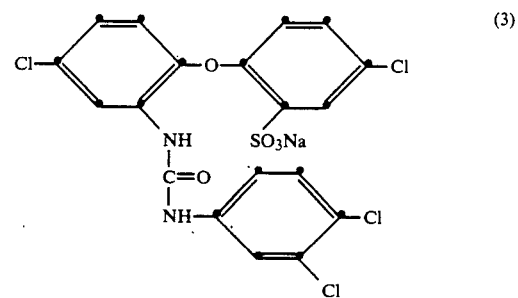

19.8 parts of tallow fatty amine ethoxlated with 6-7 mols of ethylene oxide,
10.0 parts of a block polymer of propylene glycol and ethylene oxide (average molecular weight: 4,900; 80% hydrophobic groups,
20% hydrophilic groups; HLB =4),
5.0 parts of stearyl alcohol ethoxylated with 8-9 mols of ethylene oxide,
1.4 parts of an alkyl phosphoric acid partial ester,
53.0 parts of dimethyl methane phosphonate (DMMP).

In the formulation described above permethrin can be replaced by cypermethrin, the compound of the formula (3) can be replaced by the compound of the formula

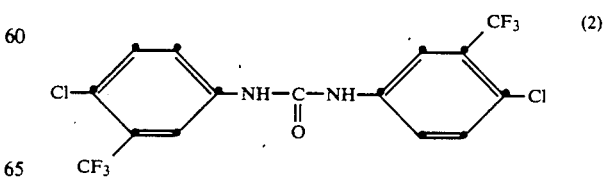

DMMP by N-methyl-2-pyrrolidone, diethylene glycol ethyl ether, ethylpolyycol or polydioles and/or alkylphenol polyglycol ether phosphate by succinic acid, lactic acid, formic acid or acetic acid. This results in formulations having similarly good properties.

EXAMPLE 3

0.6 part of permethrin
58.4 parts of 1,2-propylene glycol
1.0 part of fatty amine +ethylene oxide (Neovadin AN) are mixed. 40 parts of the compound of the formula

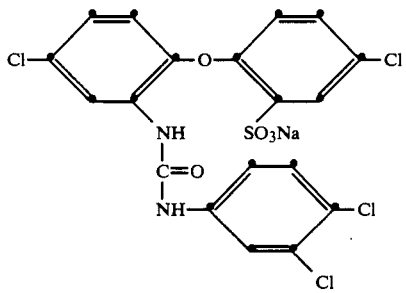 (3)

are added to this mixture with continuous stirring at 45–55° C. until a homogeneous formulation is formed. The moth-proofing formulation thus obtained has a long shelf life, is water-miscible and when applied to keratinous material produces excellent moth- and beetle-proof finishes and an especially good proofing against the seed moth (Hofmannophila pseudospretella).

EXAMPLE 4

1.0 part of permethrin
30.0 parts of dibutyl diglycol
17.0 parts of diethylene glycol monobutyl ether
27.0 parts of tributylphenol with 11 EO (ethylene oxide) are mixed. 25 parts of the compound of the formula

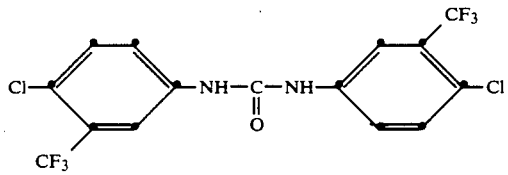 (2)

are added to this mixture with continuous stirring at 45–55° C. until a homogeneous formulatlon is formed. The moth-proofing formulation thus obtained has a long shelf life, is water-miscible and when applied to keratinous material produces excellent moth- and beetle-proof finishes and an especially good proofing against the seed moth (Hofmannophila pseudospretella).

What is claimed is:

1. An agent for proofing keratinous material against attact by larvae of carpet beetles, which contains a synergistically effective amount of (A) a diphenylurea of the formula

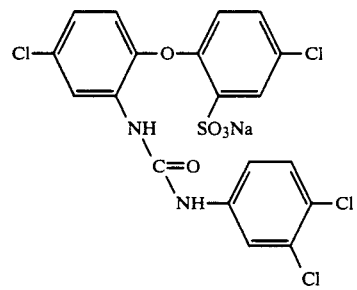

and (b) permethrin, wherein the ratio of compounds (A) and (B) is from 4:1 to 8:1.

2. A method for proofing keratinous material against attack by larvae of carpet beetles, which comprises treating the material to be proofed with an agent comprising a synergistically effective amount (A) a diphenylurea of the formula

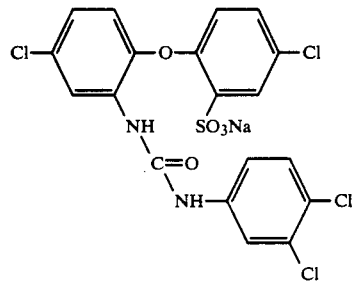

and (B) permethrin, wherein the ratio of compounds (A) and (B) in the agent is from 4:1 to 8:1.

* * * * *